United States Patent
Miller et al.

(10) Patent No.: US 9,636,247 B2
(45) Date of Patent: May 2, 2017

(54) ADJUSTABLE LORDOSIS ORTHOPEDIC INSERT FOR A BACK BRACE

(71) Applicant: Orthomerica Products, Inc., Orlando, FL (US)

(72) Inventors: John J. Miller, Apopka, FL (US); Robert B. Hamilton, III, Orlando, FL (US)

(73) Assignee: ORTHOMERICA PRODUCTS, INC., Orlando, FL (US)

( * ) Notice: Subject to any disclaimer, the term of this patent is extended or adjusted under 35 U.S.C. 154(b) by 267 days.

(21) Appl. No.: 14/490,562

(22) Filed: Sep. 18, 2014

(65) Prior Publication Data

US 2016/0081841 A1    Mar. 24, 2016

(51) Int. Cl.
*A61F 5/02*    (2006.01)

(52) U.S. Cl.
CPC ........ *A61F 5/024* (2013.01); *A61F 2250/006* (2013.01)

(58) Field of Classification Search
CPC .......... A61F 5/028; A61F 5/024; A61F 5/026; A61F 5/03; A61F 13/14; A61F 2250/006; A61F 5/0585; A61F 5/0111
USPC .......................................................... 602/19
See application file for complete search history.

(56) References Cited

U.S. PATENT DOCUMENTS

| | | | |
|---|---|---|---|
| 2,453,370 A | 11/1948 | Hittenberger | |
| 3,351,053 A | 11/1967 | Stuttle | |
| 5,449,338 A * | 9/1995 | Trudell | A61F 5/024 602/19 |
| 5,718,670 A | 2/1998 | Bremer | |
| 5,782,782 A | 7/1998 | Miller | |
| 6,702,770 B2 | 3/2004 | Bremer et al. | |
| 2001/0008955 A1 | 7/2001 | Garth | |
| 2012/0022420 A1 * | 1/2012 | Sandifer | A61F 5/026 602/19 |

* cited by examiner

*Primary Examiner* — Ophelia A Hawthorne

(57) ABSTRACT

An adjustable lordosis orthopedic insert and method of adjusting the lordosis orthopedic insert for an anatomy of a patient has a first support member configured to support a lordosis of a user's spine and a second adjustable member permanently connected to the first support member. The second adjustable member also has a relatively movable other end with a plurality of lordotic position settings to match corresponding first support member lordotic attachment positions to enable the first support member to conform to a desired setting angle. Fasteners extend through the first support member and the second adjustable member to permanently fix one of the plurality of lordotic position settings to configure the first support member at the desired lordosis setting angle. When appropriately adjusted to a setting angle, the lordosis orthopedic insert can be mounted within the flexible padded covering member for fixation to an appropriate back.

16 Claims, 11 Drawing Sheets

ADJUSTABLE LORDOSIS ORTHOPEDIC INSERT FOR A BACK BRACE

BACKGROUND OF THE INVENTION

1. Field of the Invention

The present invention is directed to an adjustable lordosis orthopedic insert that can be removably mounted within a back brace, to limit motion and provide a patient with maximum comfort and effective back support. Generally lordosis refers to a normal inward curvature of a patient's lumbar and cervical regions of the spine and is a physiological feature of a human skeleton to assist in providing an efficient walking gait for humans over that of other primates. Various factors may contribute to muscle pain or spasms that can occur, for example, in the abdominal muscles or muscles in the lumbar, spine and hamstring, resulting in an imbalance. A back brace with a customized adjustment of support for the lordosis can assist in minimizing stresses on the intervertebral disks that can be subjected to excessive secondary curvature of the lordosis in a human spine.

2. Description of Related Art

Orthotists and medical practitioners frequently have to customize an orthotic device to meet the specifics of a patient's setting angle of lordosis. In extreme cases, a cast can be made of the patient and the orthotic back brace can be made from the cast for the specific size and condition of the individual to maintain the stability of the patient's spine. Back braces can be formed with plastic inserts positioned within a relatively flexible fabric pocket. The inserts, including a lordosis insert to be positioned adjacent the spine, are then further customized usually by the application of an appropriate amount of heat and bending forces and sometimes by cutting or trimming the inserts to comply with anatomy of the particular patient. Such customizing procedures can add to the medical expense of a back brace.

SUMMARY OF THE INVENTION

The present invention enables an orthotist or a doctor to utilize an orthosis or brace having modular components that can receive and position an adjustable lordosis orthopedic insert that can be customized to conform to a specific size of a particular user to optimize performance of a brace. One example of such a brace is an adjustable orthosis that can be mounted around a waist of a user or patient in such a manner to provide a compressive force. A rear padded covering member of a configuration to receive and retain an adjustable lordosis orthopedic insert is comprised of a first support member configured to provide support for the lordosis of the user's spine and a second adjustable member connected at one end to the first support member to overlay a portion of the first support member while providing a plurality of lordotic position settings. The first support member has a plurality of lordotic attachment positions of a configuration to permit an attachment to one of the plurality of lordotic position settings to provide an appropriate setting angle of a desired lordosis configuration for the lordosis insert to support the user. Fasteners are configured to extend through the first support member and the second adjustable member when the orthotist or doctor selects one of the plurality of preset orthotic position settings appropriate for the condition of the patient or user.

The first support member and the second adjustable member are preferably flat bendable members of appropriate strength to facilitate an appropriate configuration for the particular medical condition of the patient or user. While different materials can be selected to provide the necessary flexibility and desired strength to form the first support member and the second adjustable member, flat plastic sheets with parallel front and rear surfaces can be selected and formed with appropriate apertures along perimeter configurations and a central elongated opening. The plastic sheets can be formed from a high density polyethylene with a density in the range of 0.93 to 0.97 $g/cm^2$ that can provide a higher specific strength due to the strong intermolecular forces with an appropriate tensile strength, while also having a capacity to be recycled. The flat plastic high density polyethylene (HDPE) with parallel front and rear surfaces for the first support member has an upper flexible curve perimeter portion and a lower flexible curve perimeter portion with an intermediate narrower portion connecting the upper flexible curve perimeter portion and the lower flexible curve perimeter portion. The first support member can range from a height of 13 inches to 14.5 inches or larger, depending on the size of the patient, with a thickness of ⅛ of an inch.

The second adjustable member has a height of approximately 8 inches and a width of 5 inches in the form of a rectangular configuration with curved ends and a thickness of ⅛ inch. A central rectangular opening, in the second adjustable member, matches the central opening of the first support member. The respective central elongated openings are of a dimension to overlap the user's spine and further permit the lordosis orthopedic insert to be securely fastened within a padded covering member that can be removably attached to an orthotic back brace. The padded covering member is configured with a nap surface and usually includes a foam plastic layer to soften contact with the patient's back, Hook patches of straps of one or more elongated configurations on the lordosis orthopedic insert can adhere to the nap surface of the padded covering member. The hook and nap material can be a Velcro® brand or other source of a similar configuration to enable removable attachments. This arrangement of the lordosis orthopedic insert and padded covering member also facilitates the use of an orthopedic brace having an adjustable compression feature to provide a mechanical force advantage for the user or patient when tightening the brace by altering a length of a waist component of the brace as it extends through the padded covering member without changing the desired set position of the adjustable lordosis insert in the padded covering member.

The lordosis orthopedic insert of the present invention can be customized by bending the flexible first support member to provide a desired lordosis configuration of support for the user. One end of the second adjustable member is permanently attached to the first support member with the remainder of the second adjustable member, including its other end, being unattached to the first support member. When the first support member is bent, there is a relative sliding movement of the unsecured end of the second adjustable member relative to the first support member. The orthotist or the doctor can fix an appropriate degree of bending of the first support member to achieve the desired lordosis setting angle for the particular user or patient by matching a desired orthotic attachment position on the first support member with one of the plurality of the lordotic position settings on the second adjustable member. One or more fastener members can secure the free ends of the first support member and the second adjustable member, for example with a rivet of metal or plastic that can pierce through the respective lordotic position setting and the appropriately matched lordotic support member attachment position for permanently securing the desired lordosis setting angle. With the appropriate lordosis setting angle permanently provided, the lordosis insert can be then assembled into the padded covering member for attachment to the orthotic brace.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Reference will now be made in detail to the preferred embodiments of the invention which set forth the best modes contemplated to carry out the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures and components have not been described in detail as not to unnecessarily obscure aspects of the present invention.

Figure 1:
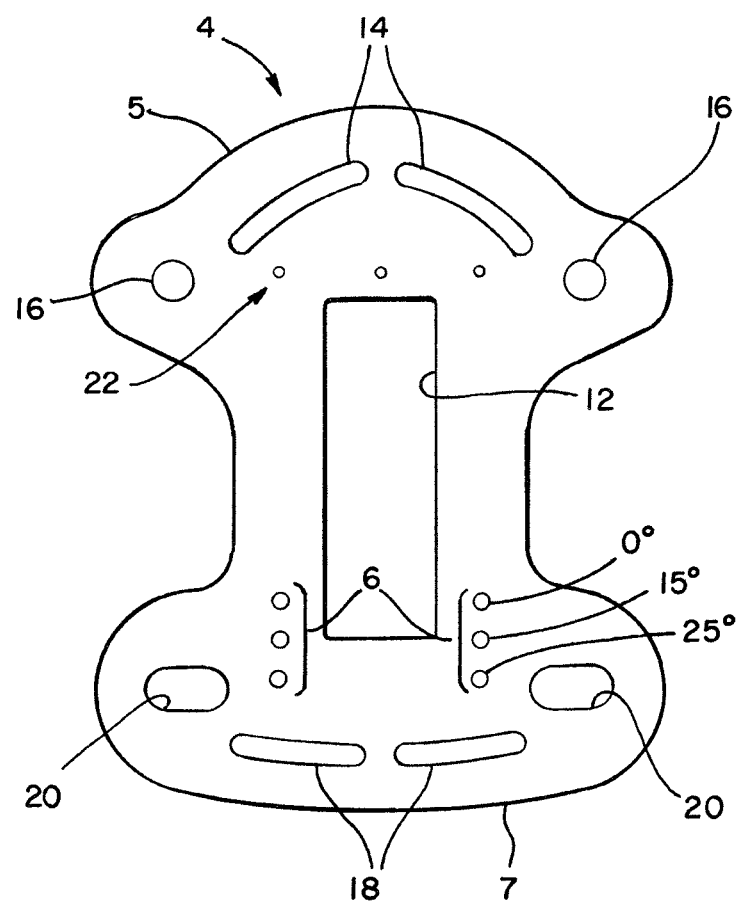
FIG. 1 is a plan view of a first support member of the lordosis orthopedic insert.

Referring to FIG. 1, a first support member 4 with attachment positions 6 comprising a pair of a series of spaced vertically positioned holes to define lordotic attachment positions 6, representative of lordosis setting angles of 0°, 15° and 25°. As can be appreciated, the specific number of holes can vary depending upon predetermined desired setting angles of the lordotic attachment positions. A central rectangular opening 12 or aperture is provided to enable a fixation of an assembled adjustable lordosis orthopedic insert 2 in an adjustable orthotic back brace, which will be described subsequently. An upper curved portion 5 includes a pair of arcuate slots 14 to provide some flexibility while a pair of small circular openings 16 further contribute to flexibility of the outer curved edges of the first support member 4. Oblong curved openings 18 provide additional flexibility in combination with the pair of elongated openings 20 in a lower curved portion 7 in addition to lowering the weight of the lordosis orthopedic insert 2.

A horizontal set of openings 22 are positioned in the top of the first support member 4 adjacent the rectangular opening 12. The pair of vertically spaced attachment position 6 are provided adjacent the bottom of the rectangular opening 12 and on either side of the rectangular opening 12.

Figure 2:
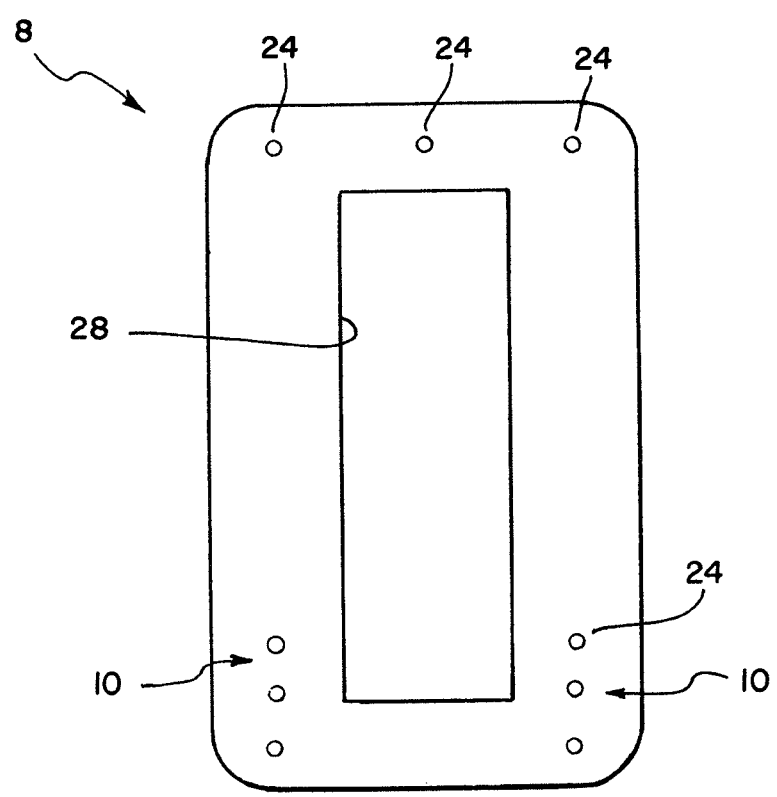
FIG. 2 is a plan view of a second adjustable member of the lordosis orthopedic insert.
Figure 3:
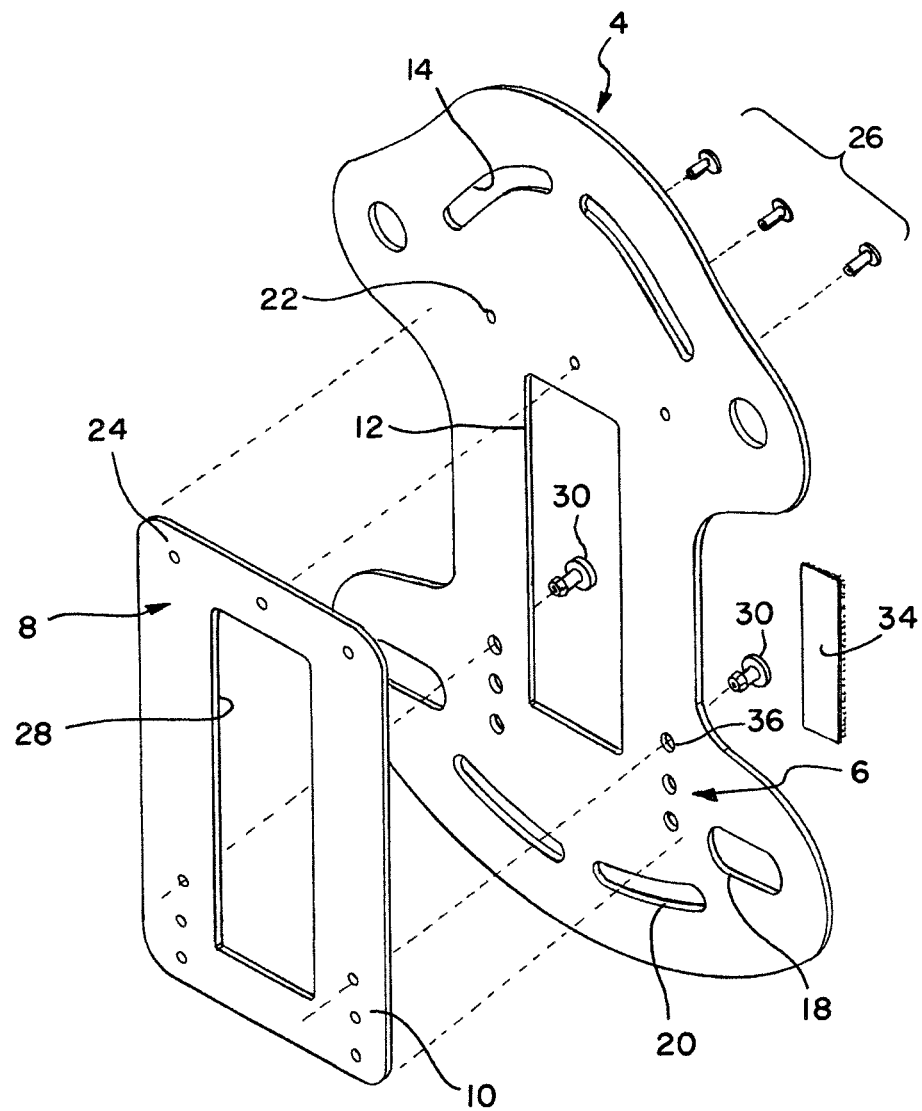
FIG. 3 is an exploded perspective view of the lordosis orthopedic insert.

FIG. 2 discloses a second adjustable member 8 with two sets of horizontally spaced vertical openings to provide a pair of lordotic position settings 10 on either side of a rectangular opening 28. Extending horizontally across the top of the second adjustable member 8 are holes 24 that will align with the openings 22 on the first support member 4. Appropriate fasteners 26 such as screws and nuts or rivets can secure the first support member 4 and the second adjustable member 8 together to align the respective rectangular opening 12 in the first support member 4 with the rectangular opening 28 in the second adjustable member 8 as shown in FIG. 3. Other types of fasteners, as known in the art, could be utilized.

Figure 6:
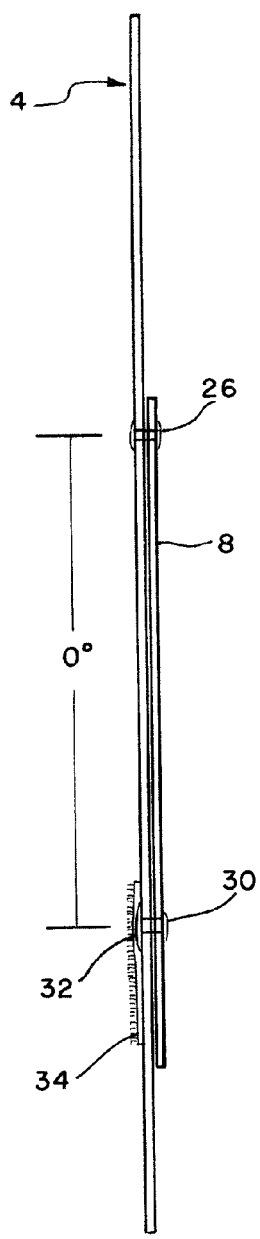
FIG. 6 is side view of the lordosis orthopedic insert with a lordosis setting angle of 0°.

The respective first support member 4 and second adjustable member 8 overlap each other and have parallel surfaces, as will be subsequently disclosed when the lordotic orthopedic insert 2 is configured to provide a setting angle of 0° for the patient or user in FIG. 6. Fasteners 30 such as, but not limited to, steel or plastic rivets, can lock the unrestrained other end of the second adjustable member 8 to the first support member 4 by inserting the fasteners 30 to maintain a parallel alignment of the matching faces of the first support member 4 and the second adjustable member 8. In the arrangement of FIG. 6, the second adjustable member 8 only provides additional strength and support to the lordosis orthotic insert 2 when configured to provide a setting angle of 0°. As can be appreciated, the upper region and the lower region of the first support member 4, extend beyond the perimeter of the second adjustable member 8, maintain flexibility to facilitate movement and comfort when in contact with the patient or user.

Figure 4:
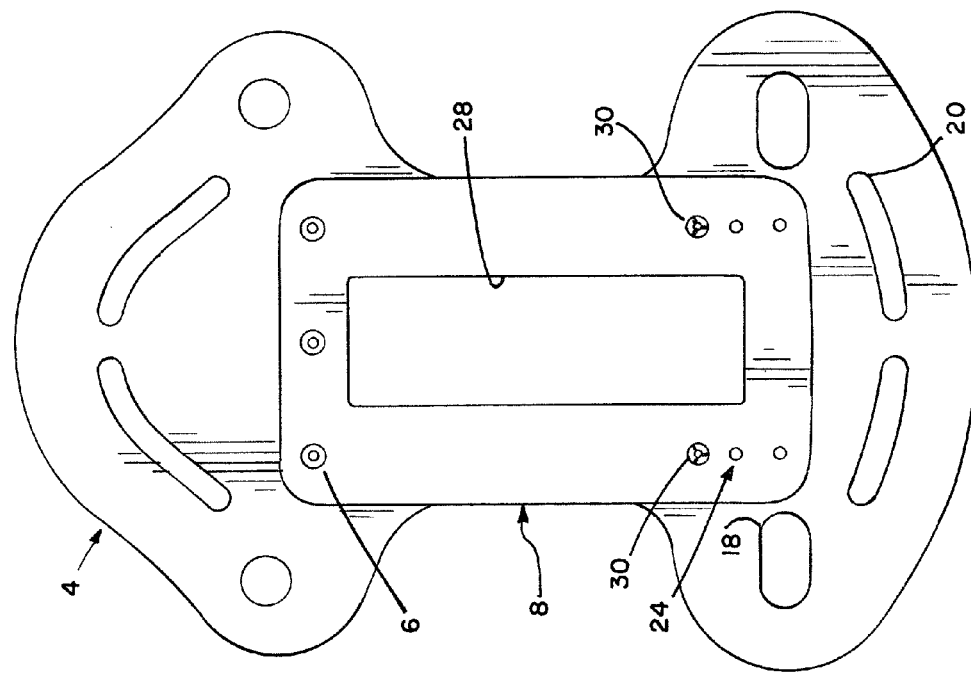
FIG. 4 is a plan view of the front of the lordosis orthopedic insert.

FIG. 4 discloses a front view of the assembled lordosis orthopedic insert 2 with the fasteners 30 in the form of rivets for setting the second adjustable member 8 and the first support member 4 to a desired lordosis configuration of a setting angle of 0°. A side view of the lordosis orthopedic insert 2 is shown in FIG. 6.

Figure 5:
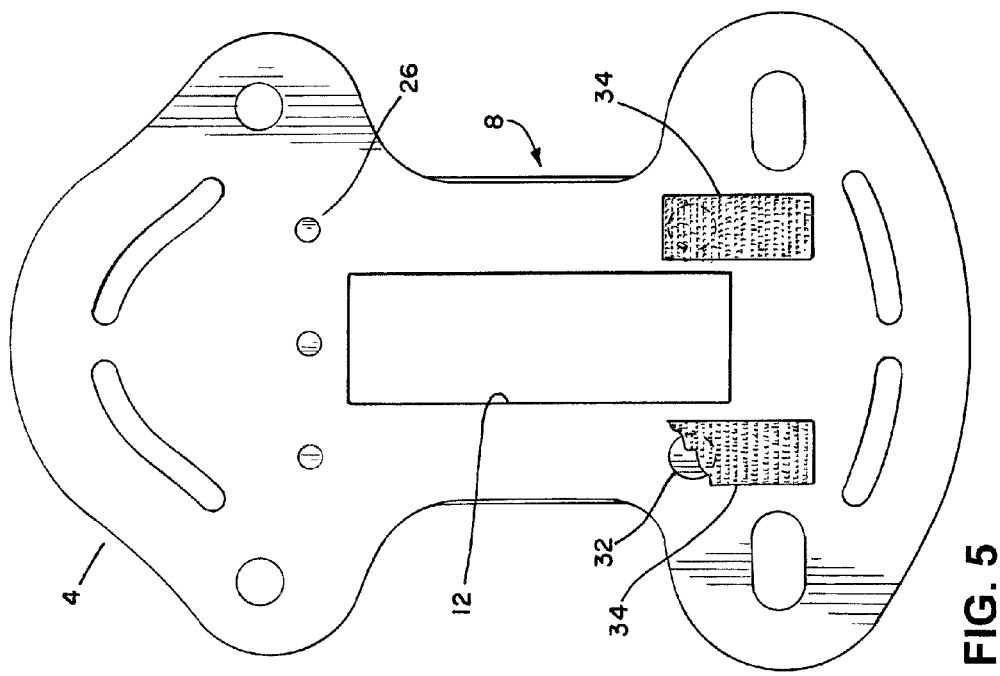
FIG. 5 is a plan view of the rear of the lordosis orthopedic insert with a partial cutaway to show an expanded fastener insert beneath a hook patch.

FIG. 5 discloses a rear view surface of the lordosis orthopedic insert 2 having a 0° setting angle with a rivet fastener head 32 expanded to lock the first support member 4 onto the second adjustment member 8, whereby respective parallel surfaces are firmly held together by the upper set of three fasteners 26. A pair of hook strips 34, for example of a type provided under the trademark Velcro® are aligned over the expanded heads 32 of the lower rivet fasteners 30 to provide an additional physical attachment to a back brace with nap material as will be subsequently described.

Figure 7:
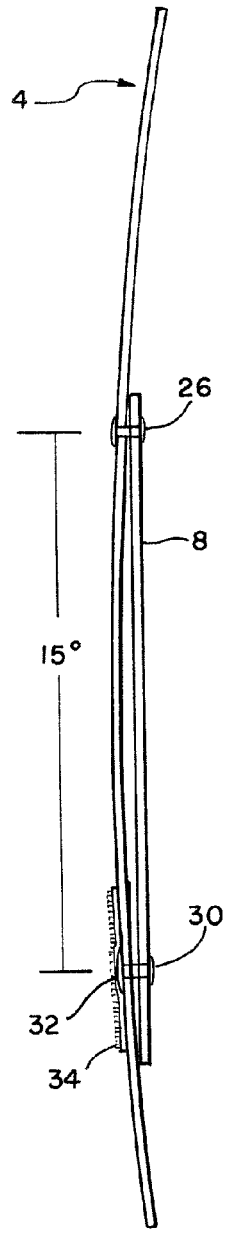
FIG. 7 is a side view of the lordosis orthopedic insert with a setting angle of 15°.
Figure 8:
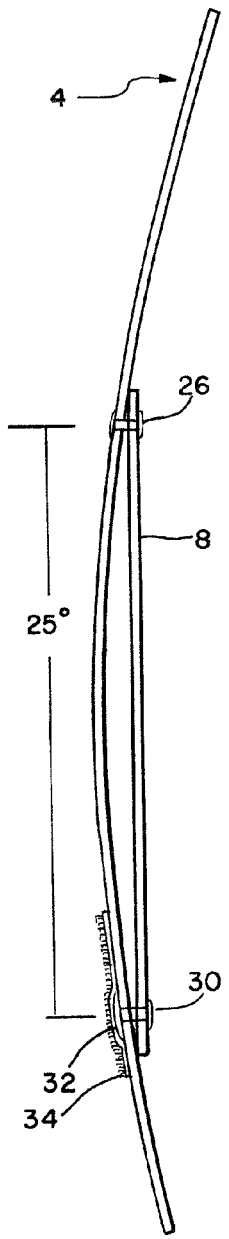
FIG. 8 is a side view of the lordosis orthopedic insert with a threading angle of 25°.

A respective setting angle of a 15° position is shown in a side view in FIG. 7 and a 25° position setting angle is shown in a side view in FIG. 8.

It should be noted that the distance horizontally between the holes 24 on the second adjustable member 8 and the holes 25 on the first support member 4 are of equal distance and enable a proper alignment of the rectangular opening 12 on the first support member 4 with the rectangular opening 28 on the second adjustable member 8. As shown in the exploded view of FIG. 3, the fasteners 26 can be utilized to firmly attach the second adjustable member 8 to the first support member 4. Alternative fasteners, besides rivets, as known in the art, can be equally utilized. The vertical distance between the top hole of the respective set of upper vertical holes 36 that form attachment positions 6 to the top hole of the lower vertical holes 24 that provides the attachment position for providing the lordotic position settings 10 are of an equal distance such as 5.821 inches and provide a lordosis 0° position setting, wherein the second adjustable member 8 will basically provide an additional strengthening of a flat planar position of the first support member 4 shown in FIG. 6.

The distance from a corresponding upper hole 22 and the middle hole of the attachment position 6 of the first support member 4 is 6.501 inches while the corresponding middle hole in the lordotic position settings 10, of the second adjustable member 8, to the upper hole 24 is 6.371 inches. As a result, a 15° position setting angle for the lordosis insert 2 is shown in FIG. 7. The lower hole 36 in the attachment position 6 of the first support member 4 is spaced a distance from the small opening holes 22 in the first support member 4 by 7.916 inches while the vertical distance to the lowest hole 24 in the second adjustable member 8 is 7.024 inches. When connected by appropriate faster or rivets 30, a lordosis angle setting of a 25° position is achieved, as seen in the rear view of FIG. 8.

As can be appreciated, by varying the respective distances, additional or different lordosis setting angles can be achieved within the ordinary skill of a person in this field. In the embodiment shown, a vertical height from the bottom to the top of the first support member 4 is 12.5 inches while the vertical height of the second adjustable member 8 is 8 inches. The thicknesses of the first support member 4 and the second adjustable member 8 is approximately 0.125 inch and the adjustable lordosis orthopedic insert 2 would have a weight of approximately 14 ounces. Since it is possible to vary the vertical height and width to meet particular patient requirements, these values are relative and can be scaled upward or downward depending on a size of a user.

Figure 9:
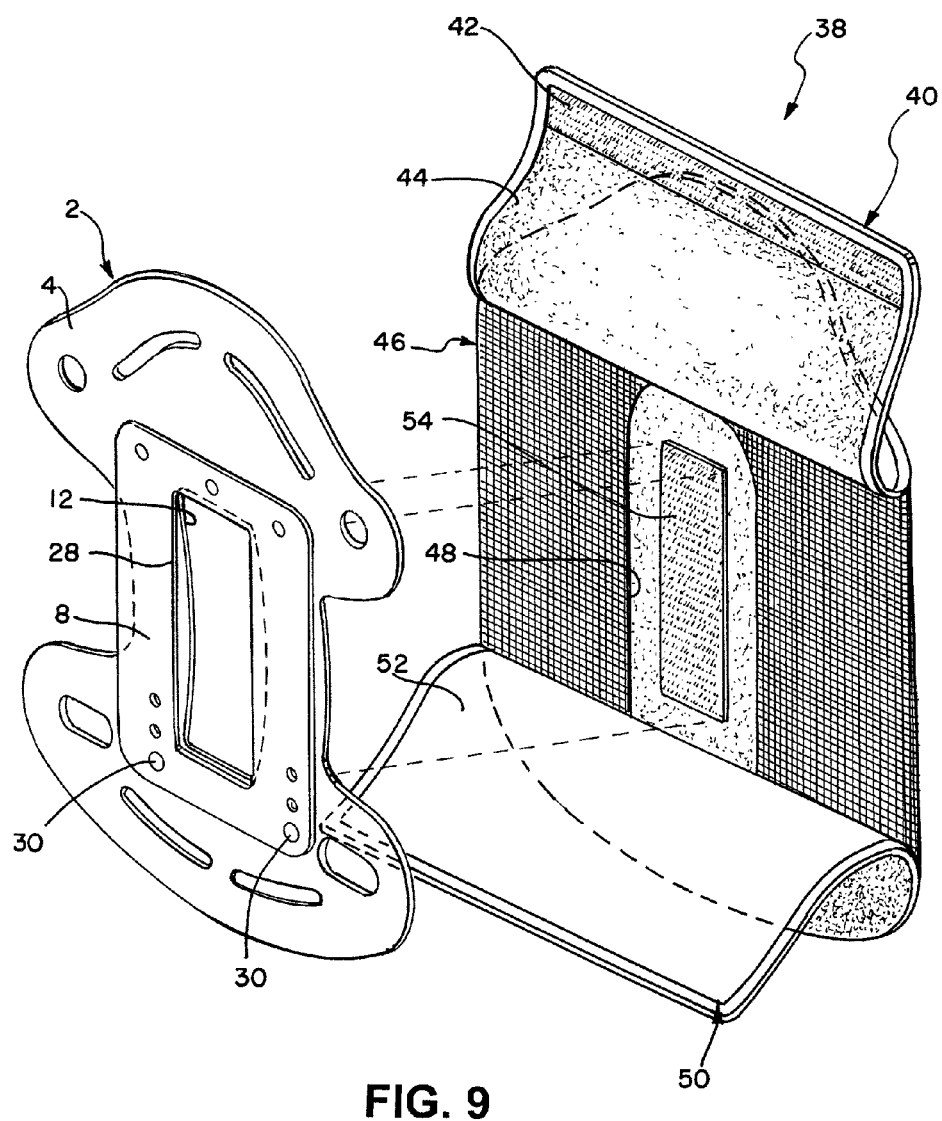
FIG. 9 is a perspective view of the lordosis orthopedic insert with a setting angle of 25° before insertion into the padded covering member.

Referring to FIG. 9, lordosis orthopedic insert 2 has been appropriately adjusted by inserting the fasteners 30 through the attachment position on the first support member 4 and through the lordotic position settings 10 in the second adjustable member 8. The padded covering member 38 is provided with an upper flap 40 having a hook fastener 42 adjacent the upper edge of the upper rear flap 40 and a lower nap surface 44. A lower rear flap 50 is provided with a relatively slidable internal surface 52 to provide a low friction surface to facilitate the movement of an adjustable back brace 56 as we further describe with regards to FIG. 12. A flexible internal cover 46 with an opening 48 also provides a relatively low friction surface while permitting the opening 48 to be stretched to receive and capture the size adjusted lordosis orthopedic insert 2. A hook retaining patch 54 is permanently attached to an internal nap surface on the padded covering member 38 beneath the flexile internal cover 46.

Figure 10:
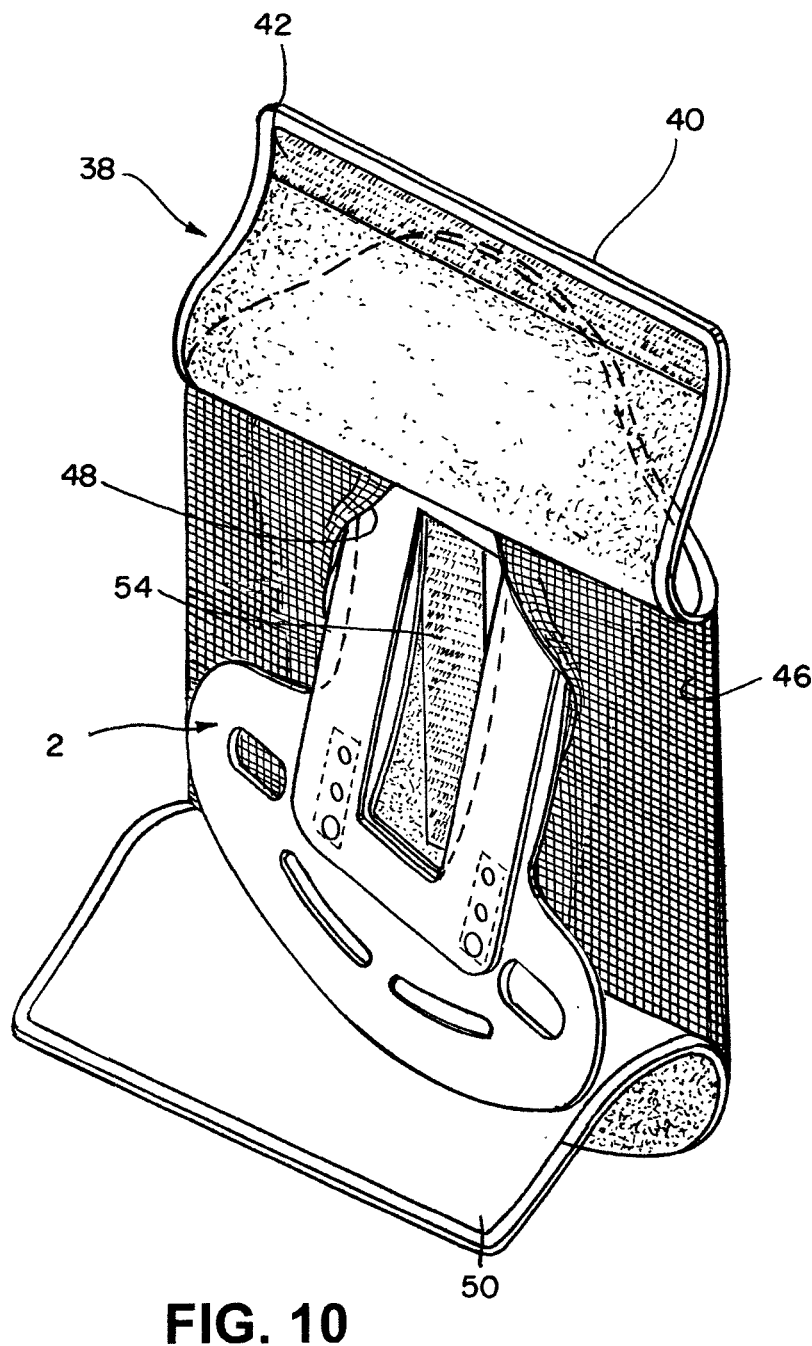
FIG. 10 is a perspective view of a partial insertion of the lordosis orthopedic insert into the padded covering member.

FIG. 10 discloses a partial insertion of the lordosis orthopedic insert 2 as it is operatively positioned within the padded covering member 38 beneath the flexible internal cover 46 or as the opening 48 is stretched.

Figure 11:
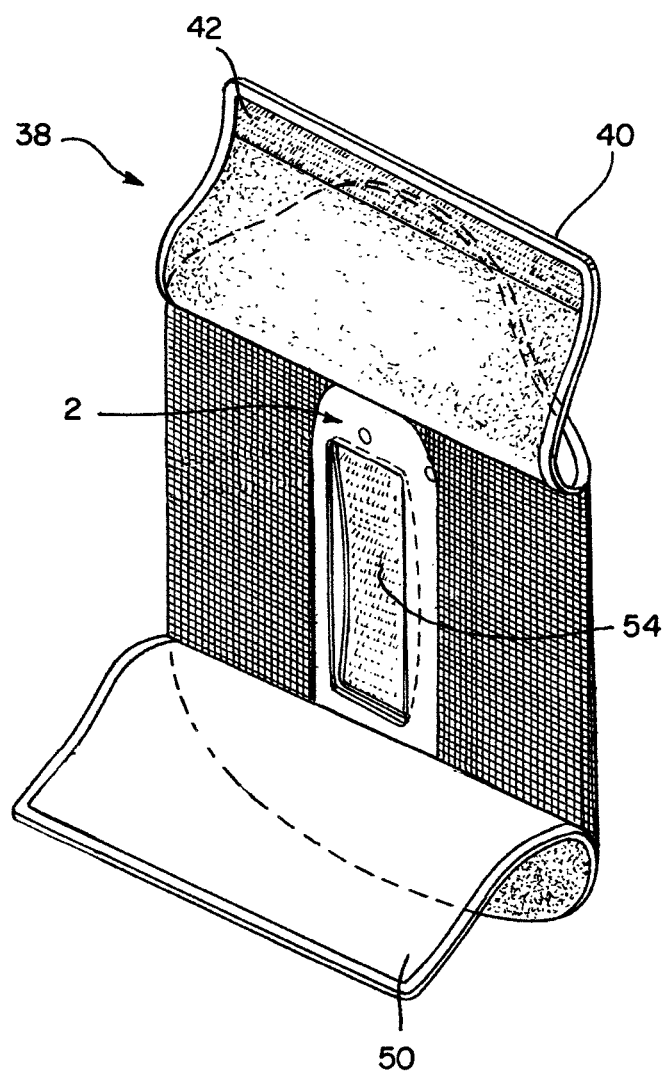
FIG. 11 is a perspective view showing the lordosis orthopedic insert fully inserted into the padded covering member.

FIG. 11 shows a perspective view of a padded covering member 38 with the appropriately adjusted lordosis orthopedic insert 2 operatively positioned so that the respective rectangular openings 12 and 28 are arranged to permit access to the hook retaining patch 54.

Figure 12:
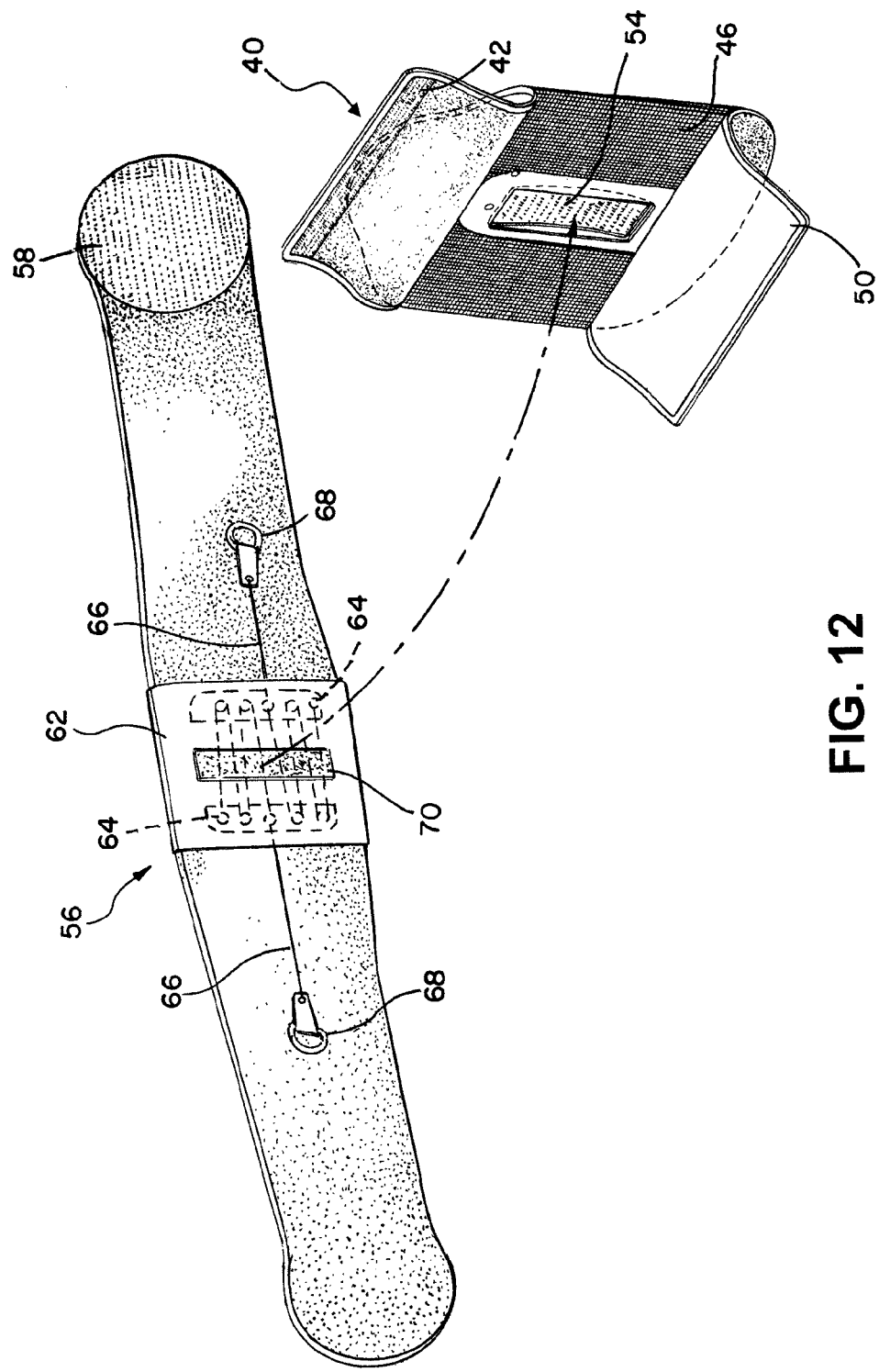
FIG. 12 is a perspective view of an adjustable orthopedic brace component disclosing an alignment of the padded covering member for an attachment to the adjustable back brace component.

An adjustable back brace 56 of a flexible configuration is disclosed in FIG. 12. The adjustable back brace 56 should be adjusted for the particular size of the patient or user and is designed to be easily mounted around the patient's waist wherein a hook material closure end 58 can be secured by overlapping complementary nap material on an exterior of the opposite side end of the back brace 56.

In the embodiment shown in FIG. 12, a central portion of the back brace 56 is provided with a flexible inner connecting pulley cover 62 and as shown in the phantom lines, a pair of respective flexible cords 66 are anchored at posts 64 to provide a force multiplying capability so that when the patient slides their thumbs into the patient closure tab 68 and pulls the respective flexible cords 66, a multiplication of the actual forces applied by the patient is used to pull the sets of posts 64 together within the flexible pulley cover 62 and provide a magnification of compression force as desired by the patient. Mounted on the exterior of flexible pulley cover 62, in a central location, is a nap fastening strip 70.

The flexible padded covering member 38 with the appropriately customized lordosis orthopedic insert 2 with a desired setting angle can be appropriately mounted so that the retaining patch 54 that is accessible between the respective rectangular openings 12 and 28 can be aligned with and attached to hold the padded covering member 38 with an alignment appropriate for the spine of the patient. The lower rear flap 50 is positioned against the exterior surface of the adjustable back brace 56. The upper rear flap 40 with the hook fastener 42 is attached to the nap surface on the outside of the lower rear flap 50 to encapture the central portion of the adjustable back brace 56 so that the positioning of the lordosis orthopedic insert 2, set to the appropriate lordosis setting angle, is mounted to support the patient's lumbar area of the spine. The choice of material utilized with regards to the padded covering member 38 and its relationship with the flexible pulley cover 62 permits the laterally extending portions of the brace to be pulled together when the patient or user extends the closure tabs 68 so that any relative movement, in contracting or expanding, to provide the appropriate compressive force does not alter the operative position of the padded cover member 38 and conversely the desired position of the lordosis orthopedic insert 2.

Figure 13:
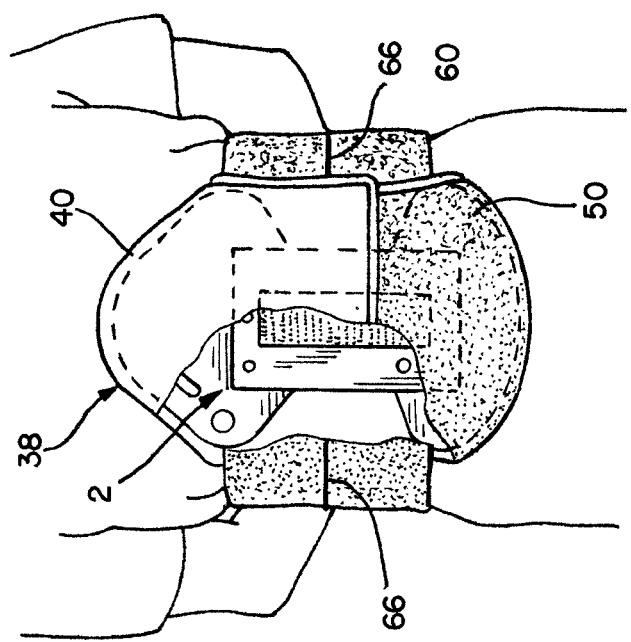
FIG. 13 is a rear view of the adjustable back brace with a cutaway of the padded covering member to disclose the lordosis orthopedic insert in dotted lines relative to the user's back.

FIG. 13 discloses a rear view of the padded covering member 38 and the adjustable back brace 56 on a patient.

Figure 14:
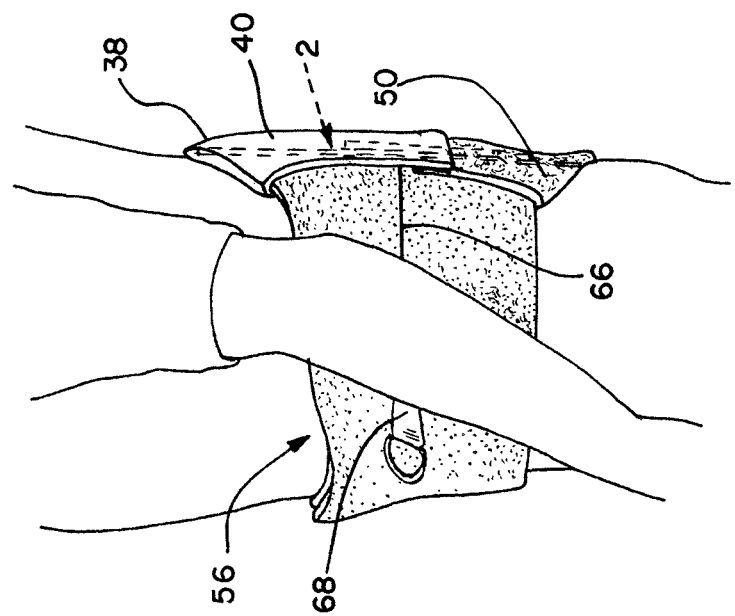
FIG. 14 is a side view of the orthopedic back brace with dotted lines showing the position of the lordosis orthopedic insert within the padded covering member.

FIG. 14 represents a partial side view of the patient and the relationship of the padded covering member 38 with the internal lordosis orthopedic insert 2 relative to the patient's spine. The flexible pulley cords 66 can be held in place by hook material on the inner sides of each of the patient closure tabs that can adhere to the nap outer surface of the adjustable back brace, as shown in FIG. 14.

Figure 15:
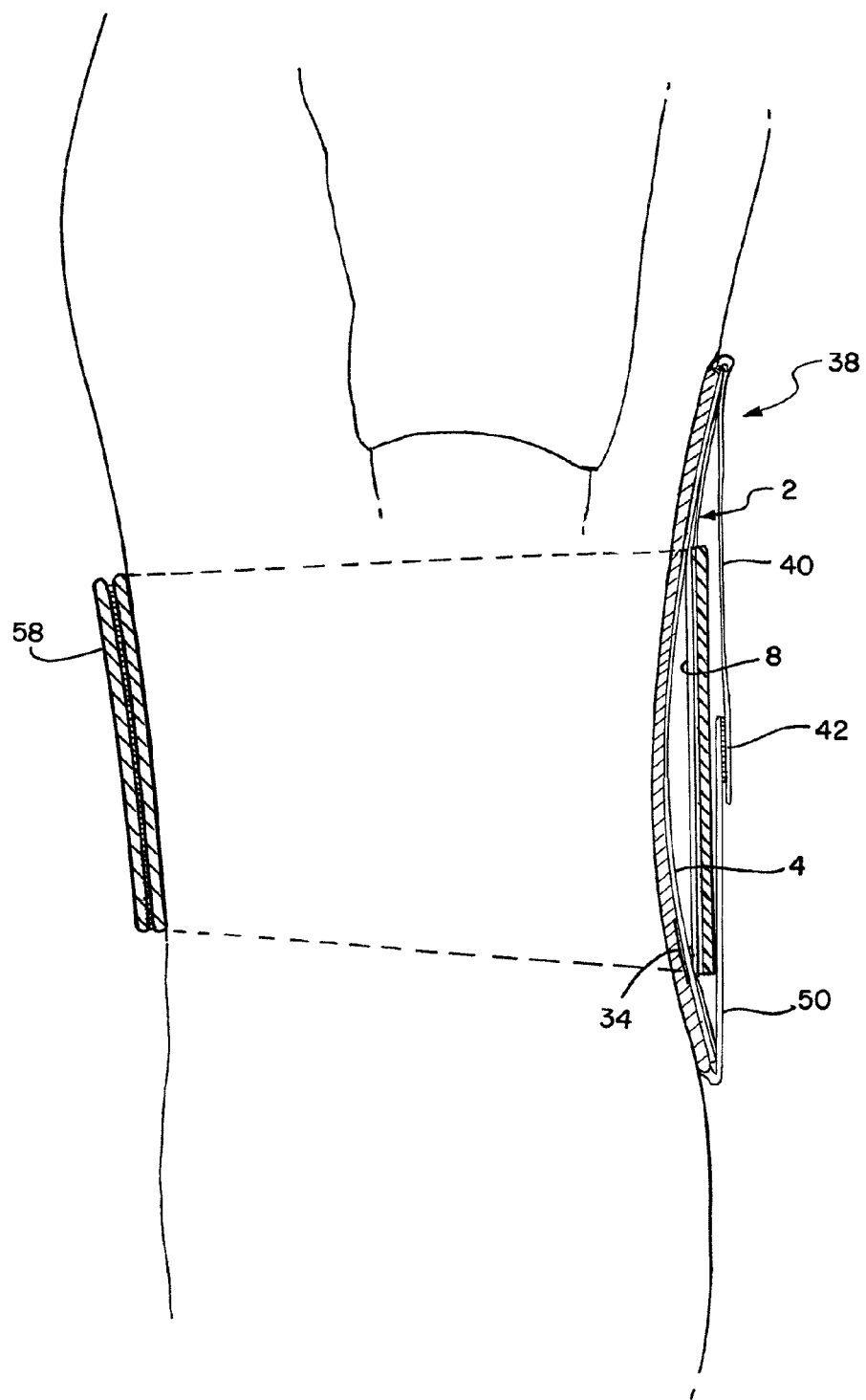
FIG. 15 is a cross-sectional view of the orthopedic back brace and padded covering member showing the location of the lordosis orthopedic insert.

FIG. 15 discloses a cross-sectional view taken from a side of the patient where the waist hook closure end 58 overlaps the other napped exterior surface of the adjustable back brace 56 with the padded covering member 38 having the lordosis orthopedic insert 2 with a setting angle of 25° appropriately positioned on the lumbar region of the spine of the user. The upper rear flap 40 is attached by the hook fastener 42 to the nap outer surface of the lower rear flap 50. As can be seen, the first support member 4 is held at the appropriate lordosis setting angle of 25° by the second adjustable member 8.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

What is claimed is:

1. An adjustable lordosis orthopedic insert for an orthotic back brace comprising:
    a first support member configured to provide support for a lordosis of a user's spine;
    a second adjustable member connected at one end to the first support member and having, adjacent the other end, a plurality of lordotic position settings, wherein a corresponding first support member lordotic attachment positions are configured for attachment to one of the plurality of lordotic position settings to enable a configuration of the first support member to conform to a setting angle between 0° to 25° to apply a desired lordosis configuration support for the user;
    a fastener for extending through the first support member and the second adjustable member to permanently attach one of the plurality of lordotic position settings with one of the support member attachment positions, wherein the first support member and the second adjustable member are flat plastic members with respective parallel front and rear surfaces, the first support member has an upper flexible curved perimeter portion and a lower flexible curved perimeter portion with an intermediate narrower portion interconnecting the upper flexible curved perimeter portion and the lower flexible curved perimeter portion, the second adjustable member has a permanent securement to the upper flexible curved perimeter portion, while the remainder of the second adjustable member overlaps the intermediate narrower portion to enable a relative sliding adjustment movement whereby the first support member is bent to the desired lordosis configuration for the user, wherein
    the intermediate narrower portion has a central elongated opening of a dimension to overlap the user's spine and the second adjustable member has a matching opening at least corresponding to the central elongated opening of the intermediate narrower portion.

2. An orthotic back brace including the adjustable lordosis orthopedic insert of claim 1 comprising:
    the padded covering member is flexible with an upper flap, and a lower flap and a flexible material covering with an opening aligned with a hook retaining patch attached to the padded covering member, the first support member has a central elongated opening of a size and location to expose the hook retaining patch when secured in the padded covering member and the second adjustable member has a matching opening to the central elongated opening, the orthotic back brace has a nap fastening strip configured to fasten the orthotic back brace to the hook retaining patch, wherein the upper flap is attached to the lower flap to capture the orthopedic back brace within the padded covering member to enable relative movement.

3. The orthotic back brace of claim 2 wherein a flexible pulley cover is attached to the nap fastening strip and the orthotic back brace to permit an adjustable movement of the orthotic back brace to apply compression pressure on the user while retaining an alignment of the adjustable lordosis orthotic insert.

4. The orthotic back brace of claim 3 wherein the orthotic back brace is adjusted to provide a mechanical multiplication of a compression force on the patient by one or more flexible cords that can be pulled by the patient to slide across posts to provide an increase or decrease in compression force on the user.

5. The adjustable lordosis orthopedic insert of claim 1 where first support member has a first elongated curved opening adjacent the upper curved perimeter portion to enable flexure and the lower perimeter portion has a second elongated curved opening adjacent the lower curved perimeter portion to enable flexure.

6. The adjustable lordosis orthopedic insert of claim 1 wherein the fastener is a rivet fastener configured into a shape to pierce into, and be retained within the first support member when inserted into one of the support member attachment positions.

7. The adjustable lordosis insert of claim 1 further including a padded covering member of a configuration to receive and retain an adjusted lordosis insert and enable an attachment to an orthotic back brace wherein the padded covering member includes one of a hook and a nap surface and the first support member includes a complimentary one of a hook and a nap surface section for adhering onto the first support surface member that contacts the padded covering member surface for positioning a removable retention of the adjustable lordosis orthopedic insert.

8. An adjustable lordosis orthopedic insert for an orthotic back brace comprising:
    a first flat support member configured to provide support for a lordosis of a user's spine, the first support member has an upper flexible curved perimeter portion and a lower flexible curved perimeter portion with an intermediate narrower portion interconnecting the upper flexible curved perimeter portion and the lower flexible curved perimeter portion, wherein the intermediate narrower portion has a central elongated opening of a dimension to overlap the user's spine;
    a second flat adjustable member matching opening at least corresponding to the central elongated opening of the intermediate narrower portion and a permanent securement at one end to the first support member and having adjacent another end of the second adjustable member, a plurality of lordotic position settings, wherein corresponding lordotic support member attachment positions on the first flat support member are configured for attachment to one of the plurality of lordotic position settings to enable a plurality of configurations of the first flat support member when the first flat support member is bent to enable relative movement of the second flat adjustable member's other end to conform to a setting angle to apply a desired lordosis configuration of support for the user, the first flat support member and the second flat adjustable member are formed of high density polyethylene plastic with parallel first and second surfaces, wherein the second flat adjustable member has a rectangular configuration with a central elongated opening of a dimension to overlap the user's spine with a first set of lordotic position settings on one side of the rectangular configuration and a second set of matching lordotic position settings on the other side of the rectangular configuration, the first flat support member and the second flat adjustable member have respective parallel front and rear surfaces before a setting of a lordotic position for a patient; and separate fasteners are provided of a configuration to be mounted in one of the corresponding lordotic positions settings, that overlap in providing a lordosis configuration, to attach the first flat support member and the second flat adjustable member to conform to a desired lordosis configuration of support for the user.

9. The adjustable lordosis orthopedic insert of claim 8 wherein the first support member has a first set of lordotic support member attached positions and a second set of matching lordotic support member positions that are positioned to receive separate fasteners when mounted on one of the corresponding lordotic position settings.

10. The adjustable lordosis orthopedic insert of claim 9 wherein the fasteners are rivet fasteners configured into a shape to pierce into, and be retained within the first flat support member when inserted into one of the support member attachment positions.

11. The adjustable lordosis orthopedic insert of claim 10 wherein the rivet fasteners are one of a metal and a plastic rivet fastener.

12. The adjustable lordosis orthopedic insert of claim 10 wherein the first flat support member has a first elongated curved opening adjacent an upper curved perimeter portion to enable flexure and a lower perimeter portion has a second elongated curved opening adjacent the lower curved perimeter portion to enable flexure.

13. The adjustable lordosis insert of claim 8 further including a flexible padded covering member of a configuration to receive and retain an adjusted lordosis insert and enable an attachment to the orthotic back brace wherein the padded covering member includes one of a hook and a nap surface and the first flat support member includes a complimentary one of a hook and a nap surface section for adhering onto a surface of the first flat support member for positioning a retention of the adjustable lordosis orthopedic insert within the flexible padded covering member.

14. A method of adjusting a lordosis orthopedic insert, for an orthotic brace, having a flexible flat first support member to provide support for a lordosis of a user and a second flat adjustable member permanently secured at one end to the first flat support member, the first flat support member having lordotic support member attachment positions and the second flat adjustable member having a plurality of lordotic position settings at a position adjacent another end of the second flat adjustable member, comprising the steps of:

bending the flexible flat first support member to provide a desired lordosis configuration of support for the user by moving the another end of the second flat adjustable member with the lordotic position settings relative to the lordotic support member attachment positions on the first flat support member until an alignment of a desired lordosis setting angle, suitable for the user, is achieved by matching an overlay of an appropriate lordotic position setting with an appropriate lordotic support member attachment position;

attaching, with a fastener, the first flat support member and the second flat adjustable member to secure a permanent alignment of the appropriate lordotic position setting and the appropriate lordotic support member attachment position; and inserting the adjusted orthopedic insert into a padded covering member of a configuration to secure and retain the adjusted lordosis orthopedic insert.

15. The method of claim 14 wherein the flexible first flat support member and the second flat adjustable member are flat plastic members that overlap and are bent and attached to permanently retain the desired lordosis configuration for the user.

16. The method of claim 15 wherein the padded covering member includes one of a hook and a nap surface and the first flat support member includes a complimentary one of a hook and a nap surface section for adhering onto a surface of the first flat support member that contacts the padded covering member surface for positioning a retention of the adjustable lordosis orthopedic insert and the attaching includes joining the hook and nap surface to secure and align the lordosis orthopedic insert within the padded covering member.

* * * * *